US009872753B2

(12) United States Patent
Yachia et al.

(10) Patent No.: US 9,872,753 B2
(45) Date of Patent: Jan. 23, 2018

(54) MEDICAL SLING WITH DETACHABLE SLING ELEMENTS

(71) Applicant: INNOVENTIONS LTD., Or Akiva (IL)

(72) Inventors: Daniel Yachia, Herzliya (IL); Valentin Ponomarenko, Haifa (IL); Ortal Netanel, Bney Brak (IL)

(73) Assignee: Innoventions LTD., Or Akiva (IL)

( * ) Notice: Subject to any disclaimer, the term of this patent is extended or adjusted under 35 U.S.C. 154(b) by 0 days.

(21) Appl. No.: 14/773,974

(22) PCT Filed: Nov. 26, 2013

(86) PCT No.: PCT/IL2013/050973
§ 371 (c)(1),
(2) Date: Sep. 9, 2015

(87) PCT Pub. No.: WO2014/091476
PCT Pub. Date: Jun. 19, 2014

(65) Prior Publication Data

US 2016/0038268 A1 Feb. 11, 2016

Related U.S. Application Data

(60) Provisional application No. 61/729,825, filed on Nov. 26, 2012.

(51) Int. Cl.
*A61N 1/36* (2006.01)
*A61F 2/00* (2006.01)
(Continued)

(52) U.S. Cl.
CPC ............ *A61F 2/0063* (2013.01); *A61F 2/004* (2013.01); *A61F 2/0045* (2013.01);
(Continued)

(58) Field of Classification Search
None
See application file for complete search history.

(56) References Cited

U.S. PATENT DOCUMENTS 6,042,534 A * 3/2000 Gellman ............... A61F 2/0045 600/30
6,896,651 B2 * 5/2005 Gross ................ A61N 1/36007 600/30

(Continued)

FOREIGN PATENT DOCUMENTS

CA 2829730 5/2008
WO WO 2010/105168 9/2010

(Continued)

OTHER PUBLICATIONS

European Patent Office, Supplemental European Search Report for U.S. Appl. No. 13/863,106, dated May 27, 2016.

*Primary Examiner* — Kennedy Schaetzle
(74) *Attorney, Agent, or Firm* — Robert G. Lev

(57) ABSTRACT

Provided is an implantable sling for supporting a body organ. The sling may be used, for example, as a urethral sling, a puborectal sling or a surgical mesh for pelvic organ prolapsed repair. The sling of the invention has a first sling element, having a first sling body and two or more slender first projections extending from the first sling body. The sling may further include a second sling element having a second sling body and two or more slender second projections extending from the second sling body, and one or more detachable connections connecting the first sling element and the second sling element. In some embodiments, the connections are configured to tear when the first and second sling elements are pulled apart.

15 Claims, 10 Drawing Sheets

109
114
113
108
110
112
112
106
111

(51) Int. Cl.
*A61N 1/05* (2006.01)
*A61N 1/378* (2006.01)

(52) U.S. Cl.
CPC ......... *A61N 1/0514* (2013.01); *A61N 1/0521* (2013.01); *A61N 1/36007* (2013.01); *A61F 2210/0076* (2013.01); *A61F 2220/0025* (2013.01); *A61F 2220/0033* (2013.01); *A61F 2220/0075* (2013.01); *A61F 2250/0001* (2013.01); *A61F 2250/0003* (2013.01); *A61F 2250/0007* (2013.01); *A61F 2250/0013* (2013.01); *A61F 2250/0063* (2013.01); *A61F 2250/0071* (2013.01); *A61N 1/3785* (2013.01)

(56) References Cited

U.S. PATENT DOCUMENTS 8,016,741 B2 * 9/2011 Weiser ............ A61B 17/00234 600/30
8,195,296 B2 * 6/2012 Longhini ............. A61F 2/0045 607/143
8,311,632 B2 * 11/2012 Pless .................... A61N 1/3785 607/35
8,751,003 B2 * 6/2014 DiUbaldi ............ A61N 1/0512 607/41
2005/0182457 A1 * 8/2005 Thrope ............. A61N 1/37211 607/48
2010/0076254 A1 3/2010 Jimenez et al.
2010/0130814 A1 * 5/2010 Dubernard ....... A61B 17/06109 600/30
2010/0198002 A1 * 8/2010 O'Donnell ........... A61F 2/0045 600/30
2010/0198003 A1 * 8/2010 Morningstar ...... A61B 17/0401 600/37
2010/0261950 A1 * 10/2010 Lund ..................... A61F 2/0045 600/30
2010/0305587 A1 * 12/2010 Straehnz ............... A61F 2/0045 606/151
2011/0112357 A1 * 5/2011 Chapman ........... A61B 17/0401 600/37
2011/0124956 A1 * 5/2011 Mujwid ................ A61F 2/0045 600/30
2011/0207992 A1 * 8/2011 Morey .................. A61F 2/0045 600/30
2011/0237867 A1 * 9/2011 Browning .......... A61B 17/0469 600/30
2011/0288368 A1 * 11/2011 VanDeWeghe .. A61B 17/06109 600/30
2015/0374408 A1 * 12/2015 Ogdahl ................. A61F 2/0045 600/30

FOREIGN PATENT DOCUMENTS

WO WO 2011/082206 7/2011
WO WO 2011/103427 8/2011

* cited by examiner

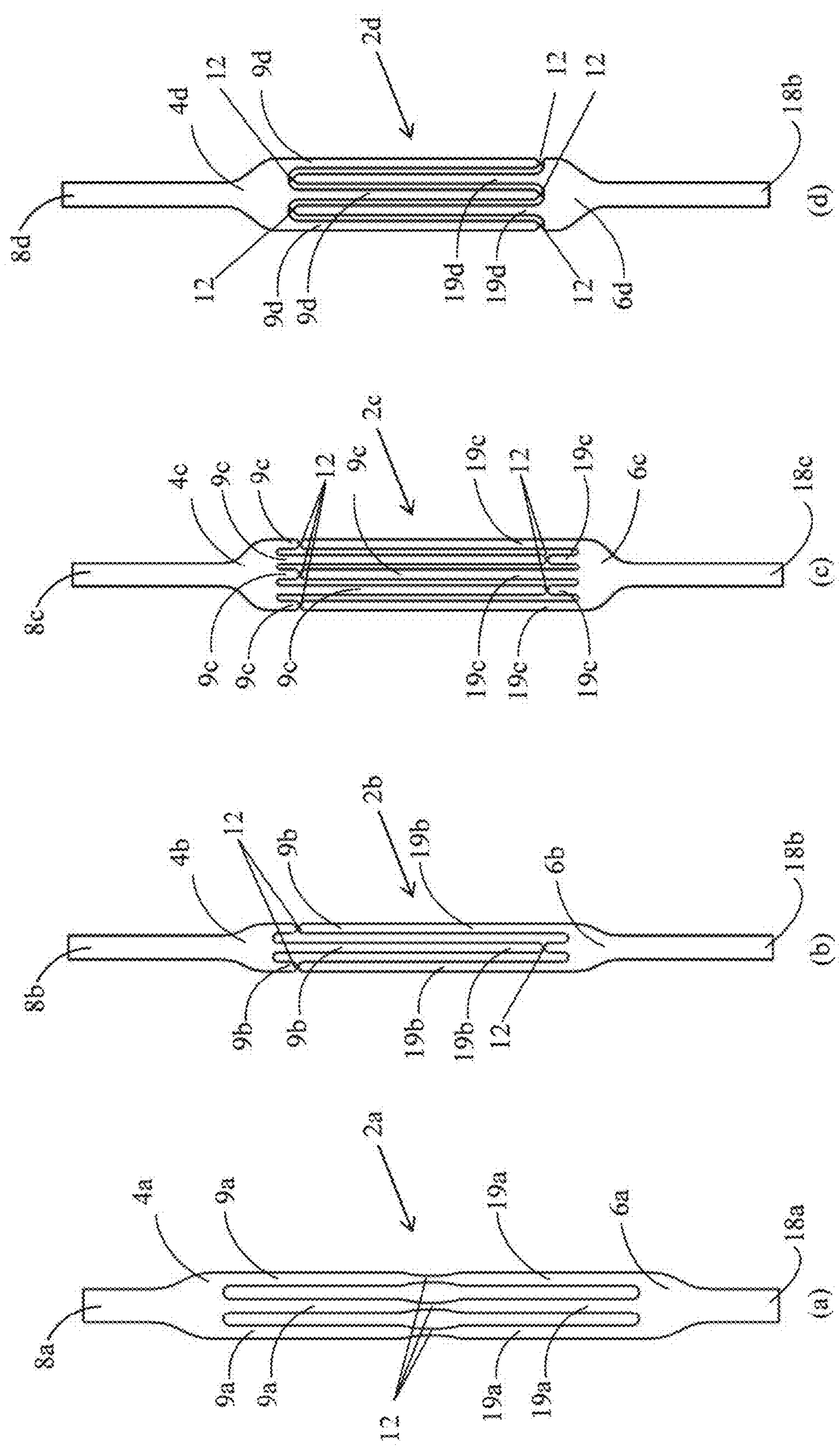
Fig. 1 (Beginning)

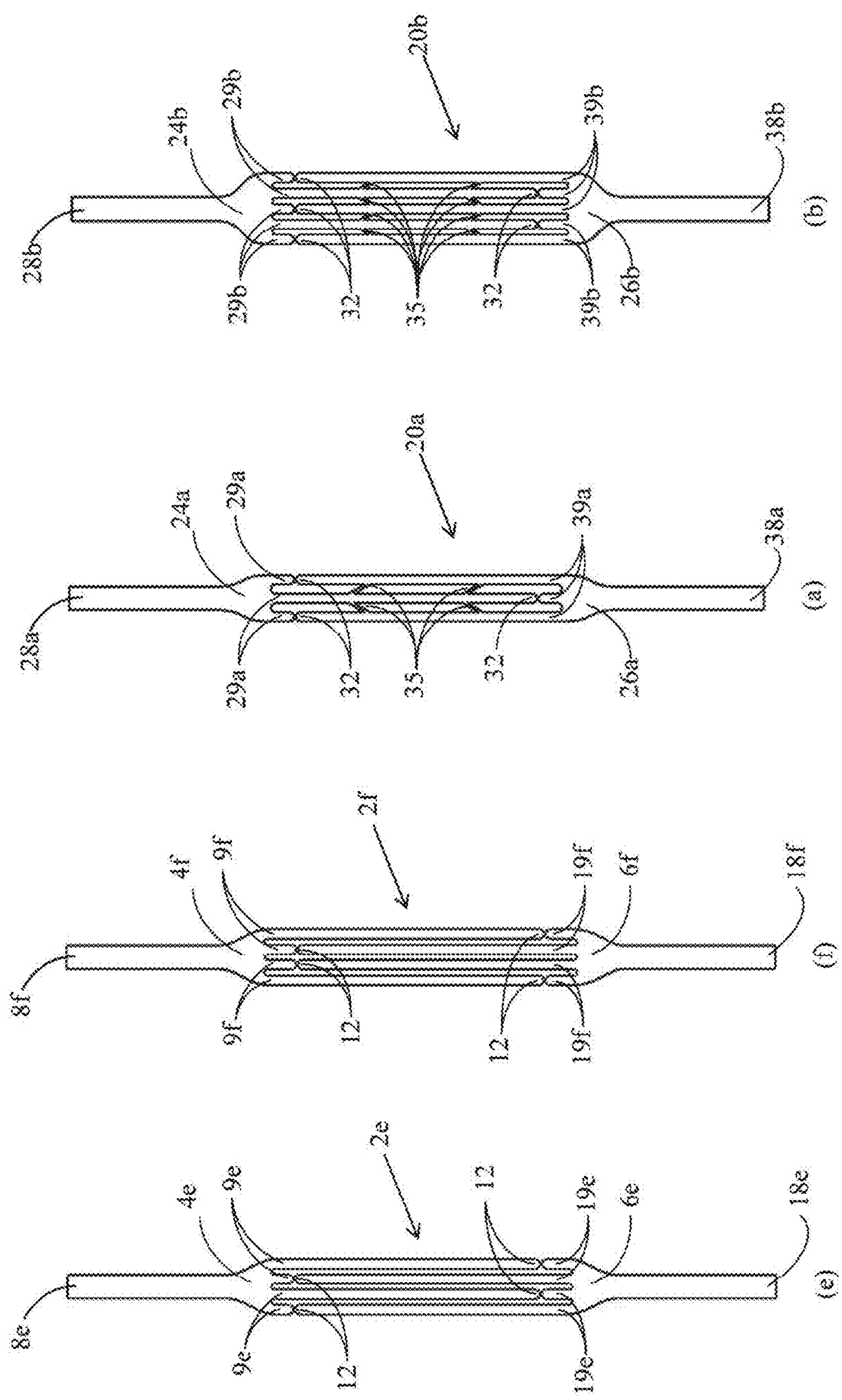
Fig. 4 (Beginning)
Fig. 1(End)

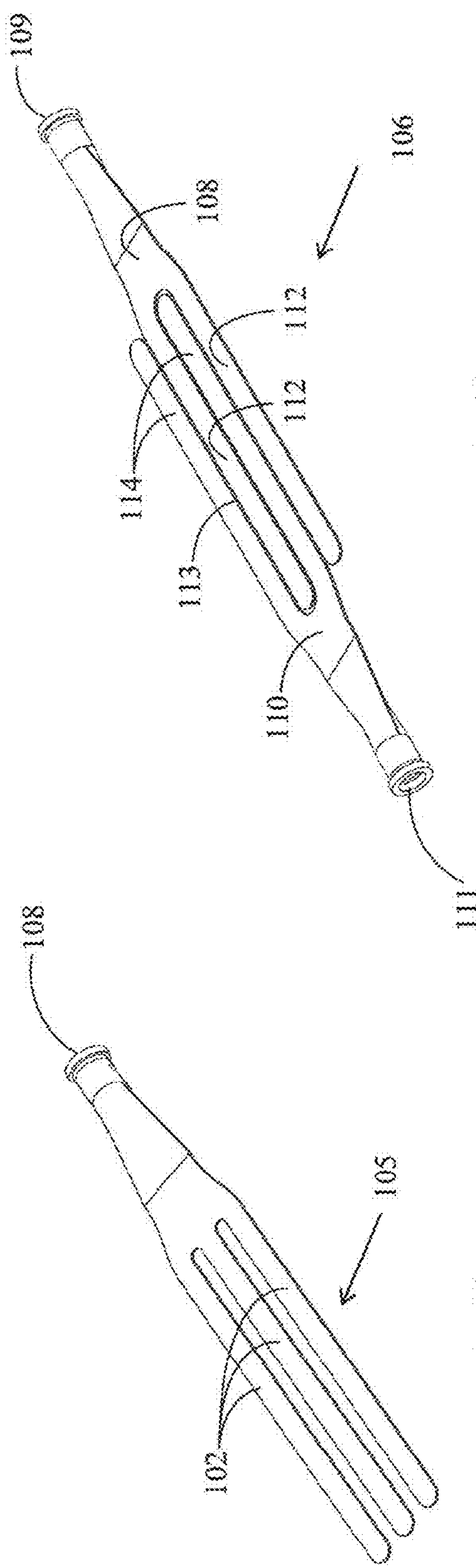
Fig. 11
Fig. 10
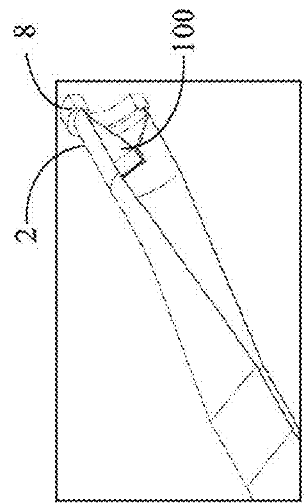
Fig. 2
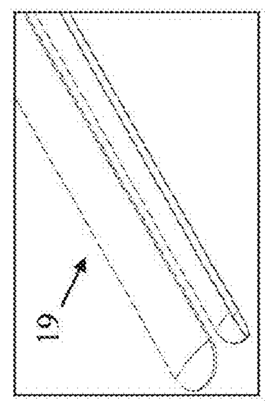
Fig. 3

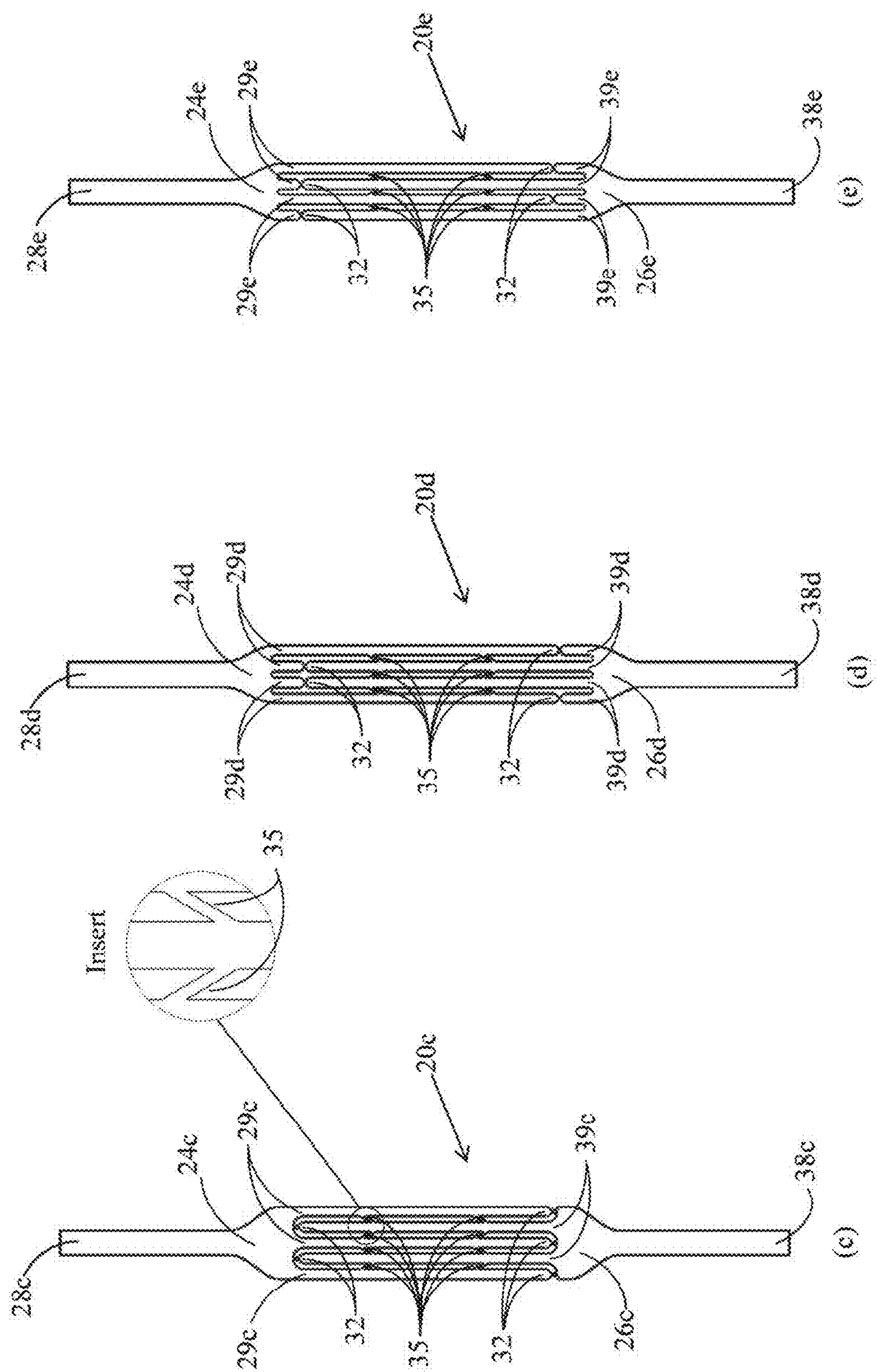
Fig. 4 (End)

46
46
42

40
48
46
42
58

20f
35
31
24f
29f
35
39f
38f
28f
29f
29f
31
31
39f
26f
(f)

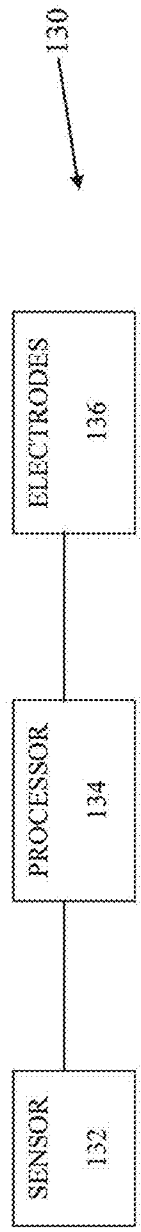
Fig. 17
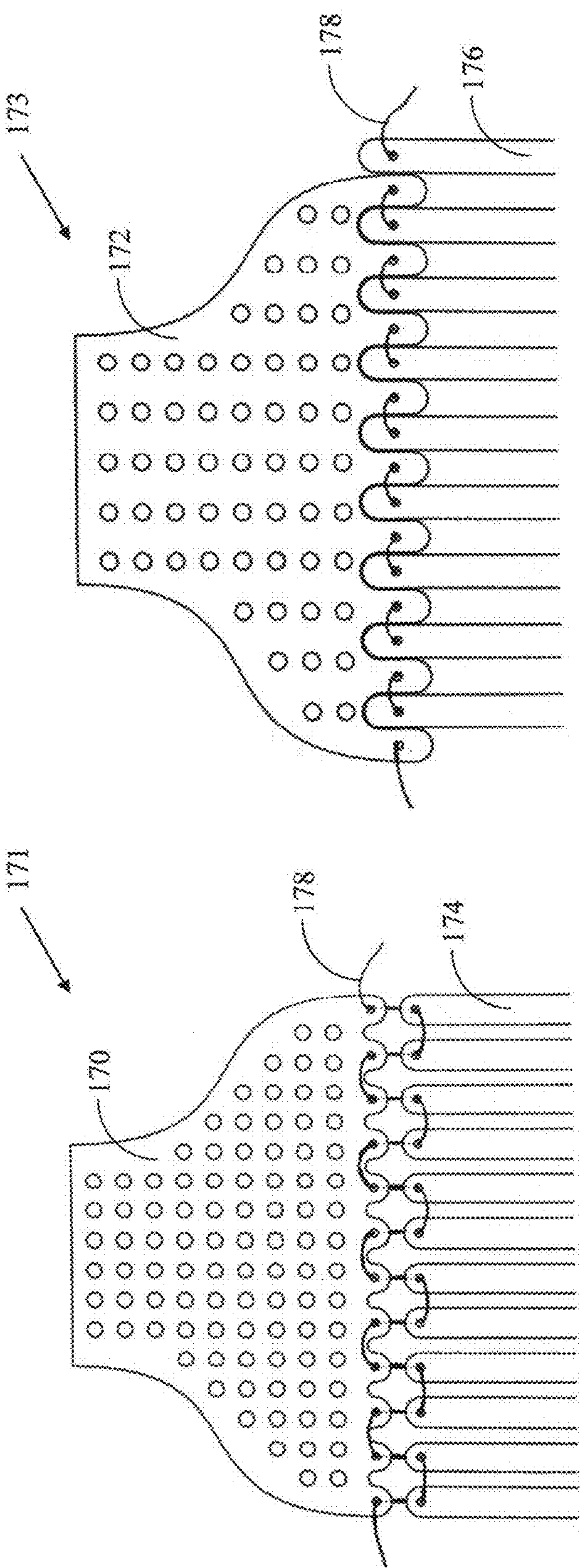
Fig. 9
Fig. 8

18a
2a 8a
120
18a
2a

8a

MEDICAL SLING WITH DETACHABLE SLING ELEMENTS

PRIORITY INFORMATION

The present application claims priority as a national stage entry of International Application No: PCT/IL2013/050973, filed on Nov. 26, 2013. The present application also claims priority from U.S. Provisional Patent Application No. 61/729,825, filed on Nov. 26, 2012.

FIELD OF THE INVENTION

This invention relates to a removable sling for use in the treatment of various conditions such as urinary stress incontinence, fecal incontinence and pelvic organ prolapse.

BACKGROUND OF THE INVENTION

Stress urinary incontinence (SUI) is the unintentional urine leakage during times of abdominal stress, such as occurs during coughing, laughing, or sneezing. One cause of SUI is inadequate anatomical support of the urethra which allows the urethra to move out of the retropubic space and rotate into the vagina. This condition is known as "hypermobility of the urethra" or simply "hypermobility". SUI may also result from insufficient closing pressure of the urethra which prevents the urethra from fully collapsing and sealing. SUI can develop in men as a result of prostate surgery during which the voluntary sphincter mechanism is damaged either partially or totally.

Another medical condition suffered by women is pelvic organ prolapse (POP) which refers to prolapse of the organs (urinary bladder, intestines and uterus) normally positioned within the pelvis. Normally these organs are supported by the "pelvic floor". Weakening of the pelvic floor allows herniation of these organs towards the vagina.

Another medical condition is fecal incontinence which is the inability to control bowel movements, causing feces to leak unexpectedly from the rectum. It may be due to a weakened anal sphincter associated with aging or to damaged nerves and muscles of the rectum and anus that can occur during childbirth.

Urethral slings have been used to treat hypermobility in women and postoperative incontinence in men. A urethral sling is typically implanted below the urethra to provide support under the urethra and prevent unwanted movement of the urethra towards the vagina or compress the male bulbous urethra. A variety of different slings have been developed that are implanted below the urethra to support it. In women, these slings are generally not intended to raise the urethra but to provide support for the urethra to prevent the unwanted downward urethral movement associated with hypermobility. A typical urethral sling comprises a strip of mesh that is implanted using a transvaginal approach in which opposite ends of the mesh are arranged on opposite sides (towards the sides or upwards) of the urethra so that the mesh loops under the urethra to form a sling. The mesh is typically implanted using needles that attach to the mesh of the sling so that the mesh ends can be inserted into the body and exit out of the body at a desired exit site and then are either anchored to the pubic bones or tissues, left under the skin, or in the periurethral or perivaginal space for self anchoring by tissue proliferation. Excess mesh extending out of the body can be removed and the remainder of the mesh left under the skin. During the first days after its implantation the unanchored sling is held in place by friction, then by tissue ingrowth through the interstices of the mesh.

POP can be repaired either by applying sutures to the pelvic floor to reshape the vagina and return the prolapsed organ to their normal position or by placing a layer of mesh to support the prolapsed organs. Surgery either through the vagina or through the abdomen (either open or laparoscopic) is the usual method of POP repair.

Fecal incontinence is treated by sphincteroplasty. Patients who are not suitable for such surgery or who have failed sphincteroplasty can be implanted a puborectal sling.

Mesh slings are generally successful in treating incontinence or POP but occasionally fail. One cause of failure is improper positioning of the sling, insufficient or excessive tension of the sling during implantation and dislocation of the sling sometime after implantation. Some of the complications which may develop after mesh implantation include failure of the sling to prevent incontinence, postoperative urine retention, sling caused bladder hyperactivity, coital pain, sexual impairment and/or discomfort, infection, vaginal and urethral tissue erosion. In some of these complications there may be an indication to remove the mesh sling. After tissue ingrowth into the spaces of the mesh, complete removal of the implanted mesh is very difficult. During the surgery or immediately after or within the first days after a mesh sling implantation, adjustment of a misplaced mesh sling can only be performed by pulling on the ends of the sling to increase the sling tension or releasing the tension through a vaginal incision. The extent of tension readjustement is limited even after a couple of weeks due to the tissue ingrowth and may not allow proper positioning of the mesh. Mesh slings do not allow late removal by simple surgery.

Some of the currently available mesh slings allow readjustment only after a few days following their implantation. United States Patent Publication 20080269547 to Hortenstine discloses an adjustable urethral mesh sling having an expansion chamber that is positioned under the urethra after implantation. A conduit in fluid communication with the expansion chamber allows remote expansion of the expansion chamber. The expanded chamber presses on the urethra and contributes to the closure of the urethral lumen during stress.

Any foreign body placed in a living tissue can elicit an inflammatory reaction in the surrounding tissue. This process is usually followed by gradual development of a cocoon-like collagen shell and/or fibrous tissue as a natural barrier around the foreign body (encapsulation). Mature cross-linked collagen and other extracellular matrix proteins gradually contribute to the formation of a hypocellular dense fibrous capsule that becomes impermeable or hypopermeable to many compounds. All soft-tissue implanted devices cause such a reaction. Since non-absorbable and biocompatible, smooth surfaced implants are unaffected by the biological activities of the surrounding tissues during the encapsulation process, they do not adhere to tissues and can be pulled-out easily at anytime. i.e. smooth surfaced monofilament surgical sutures remain within a smooth surfaced capsule and they can be pulled out at anytime much easily than a comparable multifilament braided sutures that are invaded by tissue. Other factors influencing the host response include implant location, size, shape, micromotion, surface chemistry, surface roughness, and porosity. (Dee K C, Puleo D A, Bizios R. *Wound healing. In: An introduction to tissue-biomaterial interactions*. Hoboken, N.J.: John Wiley & Sons Inc.; 2002). The process of capsule formation, as well as the structure of the final capsule, is similar in animal models and in humans. (Parker J A, Walboomers X F, Von den Hoff J W, Maltha J C, Jansen J A Soft-tissue response to silicone and poly-L-lactic acid implants with a periodic or random surface micropattern. *J Biomed Mater Res.* 2002; 61:91-98).

SUMMARY OF THE INVENTION

The present invention provides a medical sling that may be used, for example, as a urethral sling, a puborectal sling or a surgical mesh for POP repair.

The sling of the invention comprises a first sling element and a second sling element. A first set of one or more finger like projections extend from an end of the first sling element, and a second set of one or more finger line projections extend from an end of the second sling element. The first and second sling elements are integral with each other by means of a plurality of connections between the finger like projections of the sling elements that are configured to allow the first and second sling elements to separate from each other when the first and second sling elements are pulled apart. This allows the sling to be removed from the body. The sling may be removed, for example, in cases of failure of the sling to prevent incontinence, postoperative urine retention, sling caused bladder hyperactivity, coital pain, sexual impairment, discomfort, infection, vaginal and urethral tissue erosion.

The sling of the invention may be embedded between two layers of biodegradable and/or bioabsorbable mesh to facilitate fixation of the sling. The biodegradable mesh allows tissue ingrowth through its interstices and fixes the sling during the first weeks after its implantation. The mesh then disintegrates allowing the tissue to enter the longitudinal spaces along the fingers of the sling.

The sling of the invention may be made from a biostable or biodegradable polymeric material that is inelastic, soft flexible, and biocompatible. The sling material may be reinforced by a mesh or filaments embedded into a polymer. The sling may be made from a bio stable knitted or woven material that can be unraveled, or from a yarn imbedded in a smooth biostable polymer layers. The knitted material or yarns may be tightly knitted or woven with a porosity below the size of living cells to prevent tissue ingrowth into the material.

The sling of the invention may be inflatable, in which case one or both of the first and second sling elements is made from a fluid impervious material and is provided with 1 or 2 ports through which an inflation material is introduced into an interior of the sling element. The inflation material may be, for example, sterile saline.

The sling of the invention may be introduced into the body through midline vaginal incisions under the urethra and then each end of the sling is directed through its ipsilateral obturator foramine before exiting the body through a skin incision. The sling ends can have mesh-like segments for self fixation. If a trans-obturator approach is used, the mesh ends should be over the obturator fascia. If an abdominal approach is used the mesh ends should be over the rectus fascia, where the mesh tips can be reached easily to be disconnected from the removable sling, in case the sling has to be removed.

For an inflatable sling, the sling is inflated after insertion and the ports of the sling may remain beneath the skin at the level of the obturator foraminae or under the skin at the suprapubic level after implantation. At any time, the amount of inflation fluid inside the inflatable elements can be changed in order to readjust the sling tension when it is determined that the urethra is not supported in a desired manner.

When implanted, the sling of the invention may become encapsulated by fibrotic scar tissue. The sling of the invention may have a smooth outer surface which tens to prevent invasion by the surrounding tissue. Spacing between adjacent finger-like projections in the sling allows vascularization of the tissues covering the sling. After encapsulation by collagen, the sling may be removed from the body, leaving behind the encapsulation tissue which may function as an autologous sling.

At any time after implantation, the sling may be removed from the body. For removal, the first and second sling elements are detached from each other. In some embodiments, this is accomplished by grasping the ends of the first and second sling elements and simultaneously pulling the first and second sling elements apart causing the connections between the first and second sling elements to be broken. As the two sling elements continue to be pulled apart, the sling elements become separated as they are removed from the body. In other embodiments, fingers in one sling element are stitched to the other sling element by a filament. In these embodiments, the first and second sling elements are detached from each other by removing the filament, and then the two sling elements can be separated from each other by pulling the two sling elements apart.

BRIEF DESCRIPTION OF THE DRAWINGS

In order to understand the invention and to see how it may be carried out in practice, embodiments will now be described, by way of non-limiting example only, with reference to the accompanying drawings, in which:

FIGS. 1*a* to 1*f* show urethral slings in accordance with four embodiments of the invention;

FIG. 2 shows a cutaway view of an inflation port;

FIG. 3 shows details of an inflation finger in accordance with the present invention;

FIGS. 4*a* to 4*e* show urethral slings in accordance with yet another embodiment of the invention;

FIG. 7*c* shows the sling of FIG. 1*a* used as a puborectal sling;

FIG. 8 shows a unidirectional inflatable sling in accordance with another embodiment of the invention;

FIG. 9 shows a bidirectional sling in accordance with yet another embodiment of the invention;

FIG. 10 shows detail of an inflation finger of the sling of FIG. 5 or 6;

FIG. 11 shows detail of an inflation port of the sling of FIG. 5 or 6;

FIGS. 16 and 17 show attachment of sling parts with a monofilament wire.

DESCRIPTION OF THE INVENTION

Figures 5, 6A, 6B:
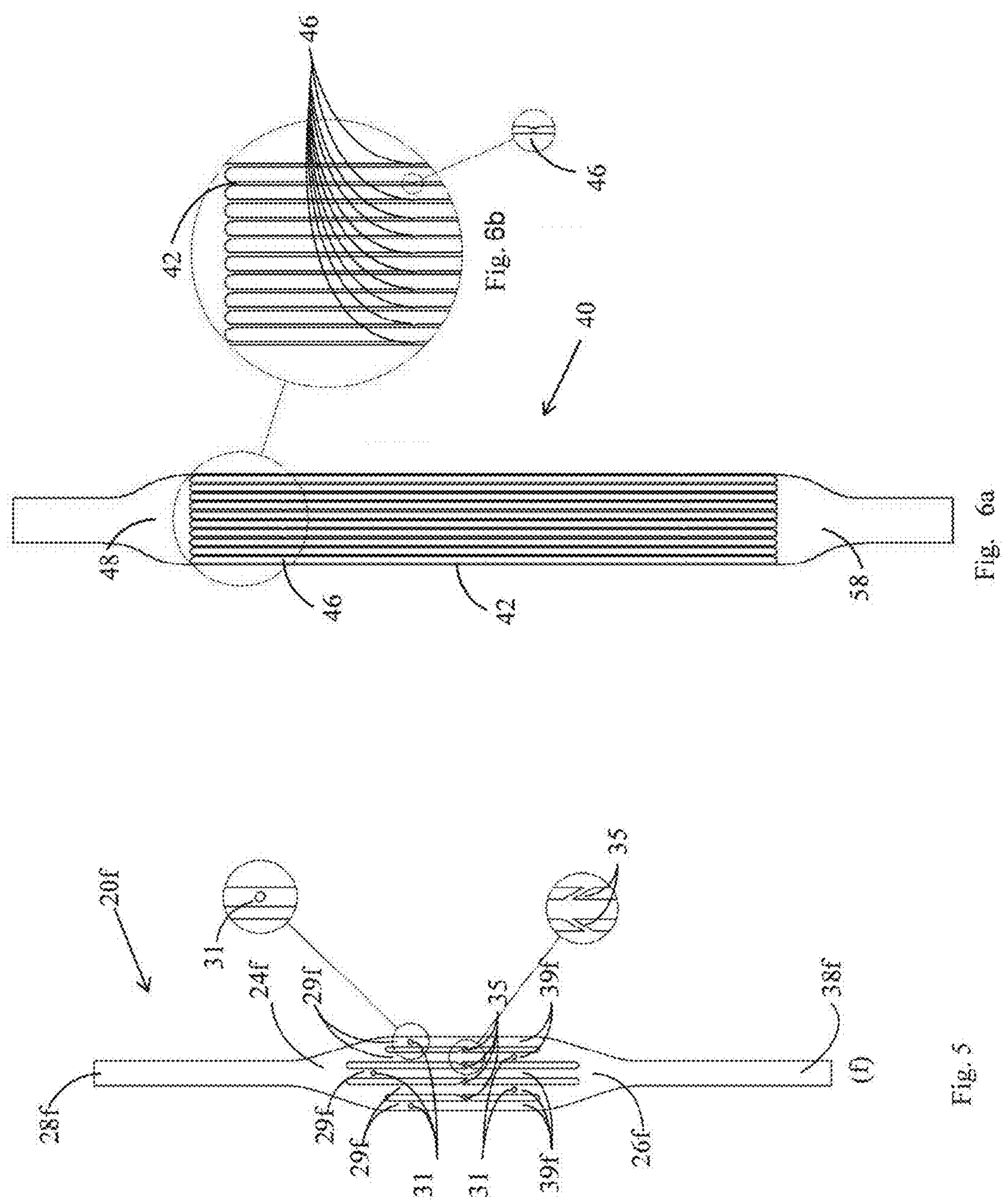
FIG. 5 shows a snap-fit attachment between layers of the sling of FIG. 13.
FIGS. 6*a* and 6*b* show a woven sling in accordance with one embodiment of the invention.

FIGS. 1*a* to 1*f* show slings 2*a* to 2*f*, respectively, in accordance with various embodiments of the invention. The slings 2*a* to 2*f* comprise a first sling element 4*a* to 4*f*, respectively, and a second sling element 6*a* to 6*f*, respectively. The first sling element 4*a* to 4*f* is provided with one or more slender finger-like projections 9*a* to 9*f*, respectively. The second sling element 6*a* to 6*f* is provided with one or more slender finger-like projections 19*a* to 19*f*, respectively. The slings 2*a* to 2*f* differ in the number and lengths of the finger-like projections. Thus, for example, in the sling 2*a*, three finger-like projections are shown on each of the elements 4*a* and 6*a*. This is by way of example only, and each element can have any number of finger-like projections as required in any application. The number of projections on the two elements may be the same, or may be different.

The first and second sling elements are integral with each other by means of a plurality of constrictions 12. The constrictions 12 are weak points in the sling and are configured to when the first and second sling elements are pulled apart, as explained below.

The slings of the invention can be made of a single layer material (non-inflatable) or double-layered (inflatable). Both the single layer and the double layer slings can be reinforced by a mesh or filaments embedded into a polymer. The slings 2*a* to 2*b* are made from a fluid impervious, biocompatible material such as silicone. The material of the slings is preferably inelastic, soft and flexible.

The sling of the invention can be either non-inflatable or inflatable. In the inflatable embodiment, as shown in the slings 2*a* to 2*f*, the first sling element is provided with a port 8*a* to 8*f* and the second sling element is provided with a port 18*a* to 18*d*, respectively. The sling is inflated by introducing an inflation material into an interior of each of the sling fingers via one or both of the ports 8 and 18. Each of the ports 8 and 18 is provided with a unidirectional valve 100, shown in the cut-away section shown in FIG. 2 which allows each element to be filled by inserting the tip of a syringe filled with the inflation material through the valve and then withdrawing the syringe from the valve. A cut-away view of an inflated finger-like projection is shown in FIG. 3. Inflation of the sling provides stiffness to the extensions for providing stiffer support to the urethra without causing additional compression to the urethra. Such an increase in stiffness can also be obtained mechanically by stretching the extensions using a flexible wire or ribbons for pushing the tips of the fingers.

FIGS. 4*a* to 4*e* show slings 20*a* to 20*e*, respectively, in accordance with five additional embodiments of the invention. The slings 20*a* to 20*e* comprise a first sling element 24*a* to 24*e*, respectively, and a second sling element 26*e* to 26*e*, respectively. The slings 20*a* to 20*e* can be either non-inflatable or inflatable. In the inflatable embodiment, the first sling element is provided with a port 28*a* to 28*e* and the second sling element is provided with a port 38*a* to 38*e*, respectively. The port may be the port 100, shown in FIG. 2, as explained above in reference to the slings shown in FIG. 1*a*. From the ports 28*a* to 28*e* extend one or more finger like projections 29*a* to 29*e*. From the ports 38*a* to 38*e* extend one or more finger like projections 39*a* to 39*e*, respectively. The slings 20*a* to 20*e* differ in the number and lengths of the finger-like projections. Thus, for example, in the sling 20*a*, three finger-like projections are shown on each of the elements 24*a* and 26*a*. This is by way of example only, and each element can have any number of finger-like projections and finger lengths as required in any application. The number of projections on the two elements may be the same, or may be different.

The first and second sling elements are integral with each other by means of a plurality of constrictions 32. The constrictions 32 are weak points in the sling and are configured to tear when the first and second sling elements are pulled apart, as explained below. In addition, the projections on the first and second sling elements are attached together at a plurality of weak lateral connections 35, shown in greater detail in the insert to FIG. 4*c*. the lateral connections 35 tend to maintain the projections 29 and 39 parallel to each other.

The slings 20*a* to 20*e* are made from a fluid impervious, biocompatible material such as silicone. The material of the slings is preferably inelastic and soft and flexible.

The slings 20*a* to 20*e* are either inflatable or non-inflatable. In the inflatable embodiment the sling is inflated by introducing an inflation material into an interior of each of the sling fingers via one or both of the ports 28 and 38. Each of the ports 28 and 38 is provided with a unidirectional valve which allows each element to be filled by inserting the tip of a syringe filled with the inflation material through the valve and then withdrawing the syringe from the valve.

FIG. 5 shows a sling 20*f*, in accordance with yet another embodiment of the invention. The sling 20*f* comprises a first sling element 24*f*, and a second sling element 26*f*. The slings 20*f* can be either non-inflatable or inflatable. In the inflatable embodiment, the first sling element is provided with a port 28*f* and the second sling element is provided with a port 38*f*. The port may be the port 100, shown in FIG. 11, as explained above in reference to the slings shown in FIG. 1. From the port 28*f* extend one or more finger like projections 29*f*. From the port 38*f* extend one or more finger like projections 39*f*. The sling 20*f* is provided with a plurality of weak points, which in this embodiment are perforations 31. The perforations 32 are configured to tear when the first and second sling elements are pulled apart, as explained below. In addition, the projections on the first and second sling elements are attached together at a plurality of weak lateral connections 35, as explained above in reference to the slings 20*a* to 20*e*, that tend to maintain the projections 29 and 39 parallel to each other.

The sling 20*f* can be made from a fluid impervious, biocompatible material such as silicone. The material of the slings is preferably inelastic and soft and flexible.

FIG. 6*a* shows a sling 40 in accordance with yet another embodiment of the invention. The sling 40 has a first end 48 and a second end 58. The first and second ends are joined by a plurality of narrow strands or fibers 42, shown in greater detail in FIG. 4*b*. In each strand are one or more of constrictions 46, shown in greater detail in the insert to FIG. 6*b*. The constrictions 46 are weak points in the sling and are configured to-detach when the first and second ends of the sling are pulled apart, as explained below. The sling 40 is not-inflatable.

Figures 7A, 7B:
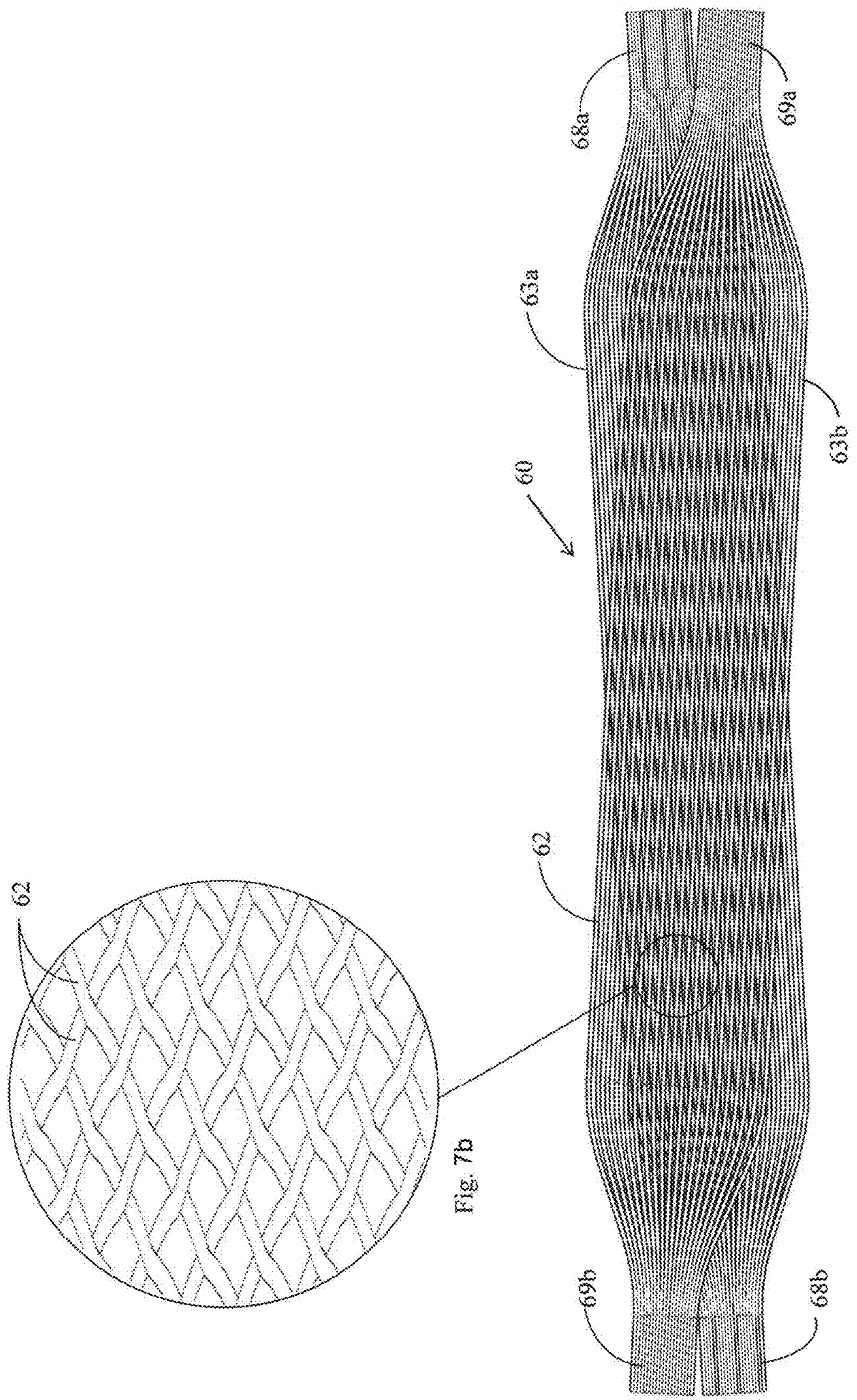
FIG. 7*a* shows the sling of FIG. 1*a* after implantation in the body using the trans-obturator approach.
FIG. 7*b* shows the pubourethral sling of FIG. 1*a* after implantation in the body either using the trans-abdominal or trans-vaginal approach (the sling becomes U-shaped)

FIG. 7*a* shows a sling 60 in accordance with till another embodiment of the invention. The sling 60 is woven from fibers 62 shown in greater detail in FIG. 7*b*. The sling 60 comprises a first sling element 63*a* having an end 68*a*, and a second sling element 63*b* having an end 68*b*. The first and second sling elements are interwoven so as to form an integral unit. The ends 68_a_ and 68_b_ may be grasped and pulled apart causing the first and second sling elements to detach from each other.

Figures 16A, 16B:
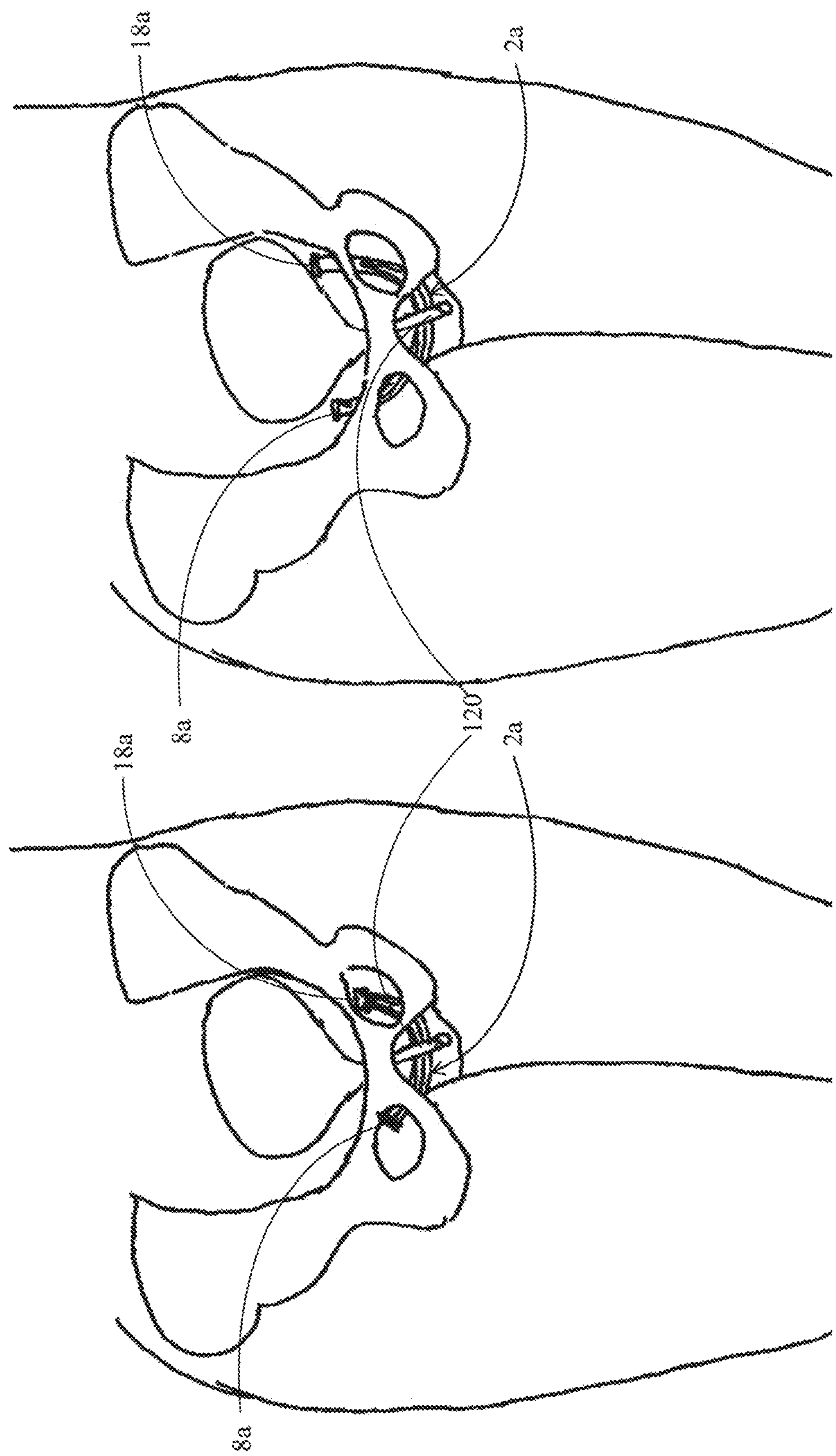
Figure 16C:
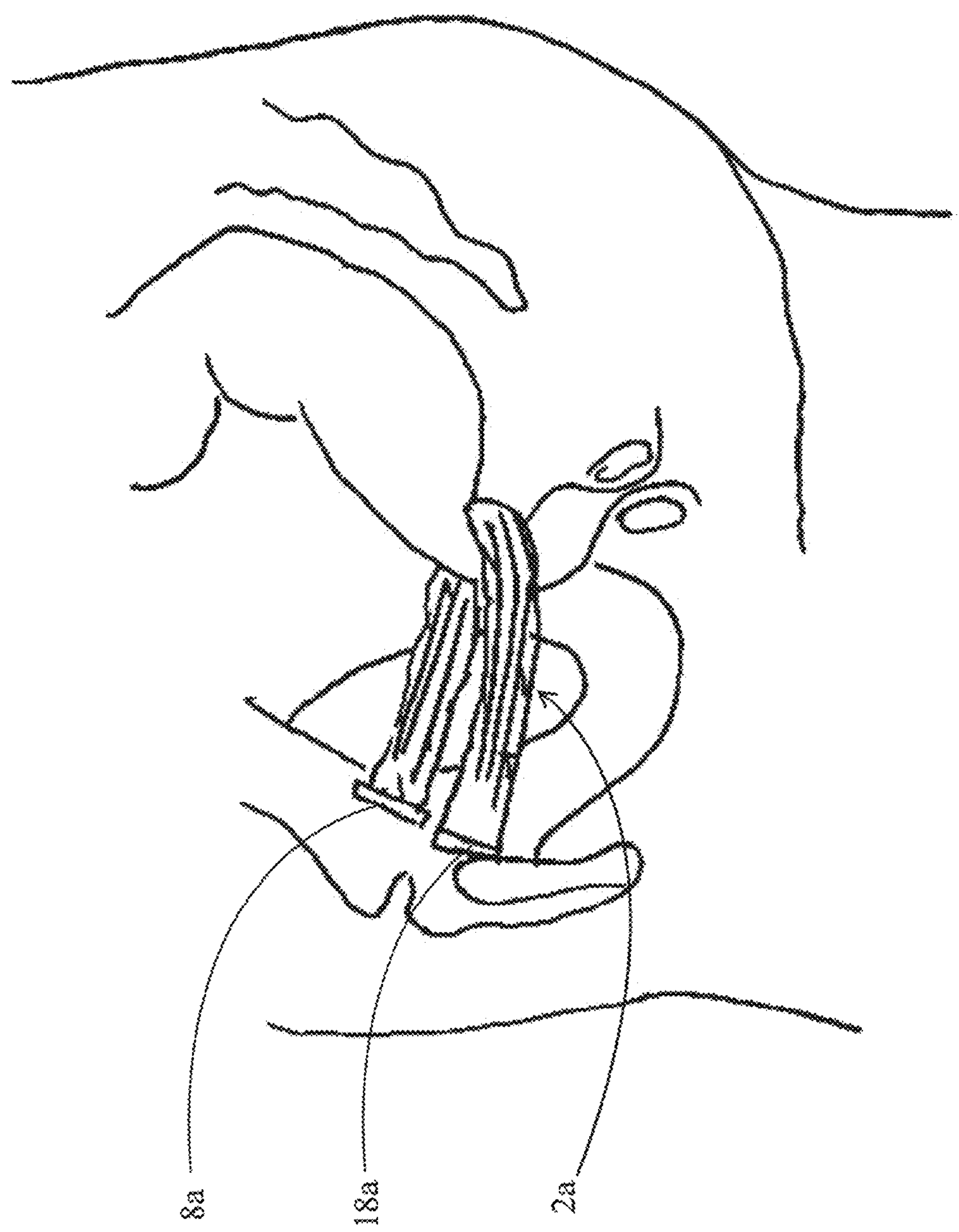

FIGS. 8 and 9 show an end 170 and 172, of a sling 171 and 173, respectively, in accordance with another embodiment of the invention. Finger-like extensions 174 and 176, respectively are attached by a monofilament wire 178 to the ends, 170 and 172, respectively, thus connecting the elements of the sling. FIGS. 16 and 17 show different connecting schemes. Pulling the end of the wire 178 which is located at the end of the sling, removes the wire 178 and releases the fingers 174 and 176 from the end, 170 and 172, respectively, allowing removal of the sling components. Alternatively, the elements of the sling may be pulled apart which pulls the wire together with one of the elements of the sling during separation.

FIG. 10 shows an inflatable sling 105 in accordance with another embodiment of the invention. The sling 105 has a single inflatable unit having three finger-like projections 102 which is inflated through a port 108. [The invention, as defined in the claims, is a sling having two parts that separate when the parts are pulled apart. It's not clear how the embodiment of FIG. 8 fits into this definition.]

FIG. 11 shows an inflatable sling 106 having two inflatable units 108 and 110. The inflatable unit 108 and 110 has an inflation port 109 and 111, respectively.

The inflatable unit 108 and 110 has two finger-like projections, 112 and 114, respectively. The projections 112 of the inflatable unit 108 are interdigitated with the projections 114 of the inflatable unit 110. [It's not clear what holds this thing together]

Figure 13:
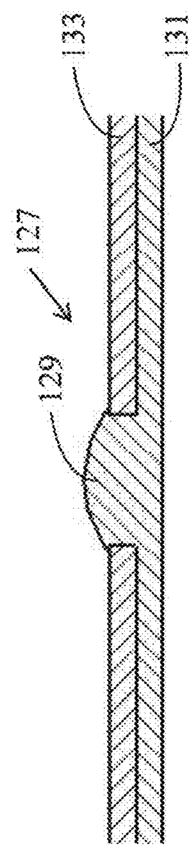
FIG. 13 shows a multilayerd mesh for use in Pelvic Organ Prolapse (POP)
Figure 12:
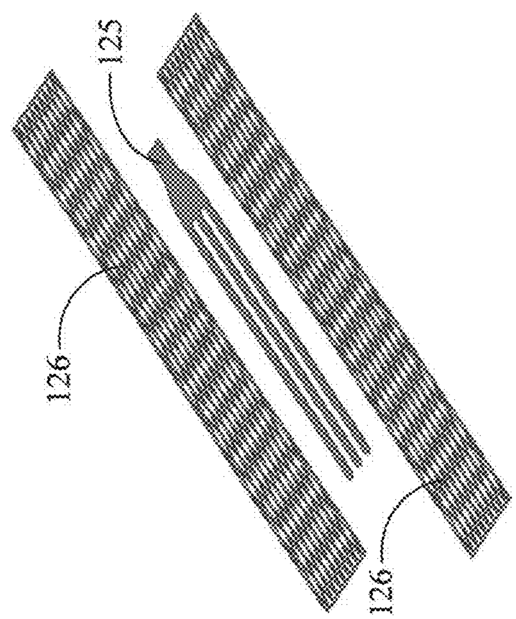
FIG. 12 shows a sling of the invention placed between two layers of biodegradable and/or bioabsorbable mesh.
Figure 14:
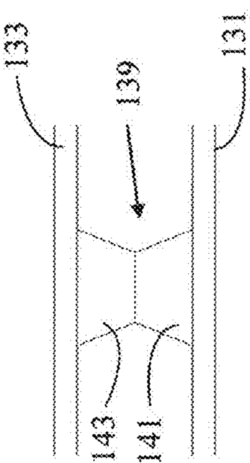
FIG. 14 shows a snap-fit attachment between layers of the sling of FIG. 13.

FIG. 12 shows embedding a sling 125 of the invention between two layers of biodegradable and/or bioabsorbable mesh 126 for early fixation of the sling. The biodegradable material allows tissue ingrowth through its interstices and fixes the sling during the first weeks after its implantation. The mesh then disintegrates allowing the tissue to enter the longitudinal spaces along the fingers of the sling. The two layers of mesh 126 may be attached to one another by means of a snap-fit attachment. In one embodiment, shown in FIG. 13, a snap-fit attachment 127, is achieved by a protrusion 129 in one layer 131 that snap-fits into a hole in the second layer 133. In another embodiment, shown in FIG. 14, a snap fit attachment 139 is formed by mated protrusions 141 and 143 extending from the layers 131 and 133 respectively. A similar attachment can be used for attaching a third or fourth layer.

Figure 15:
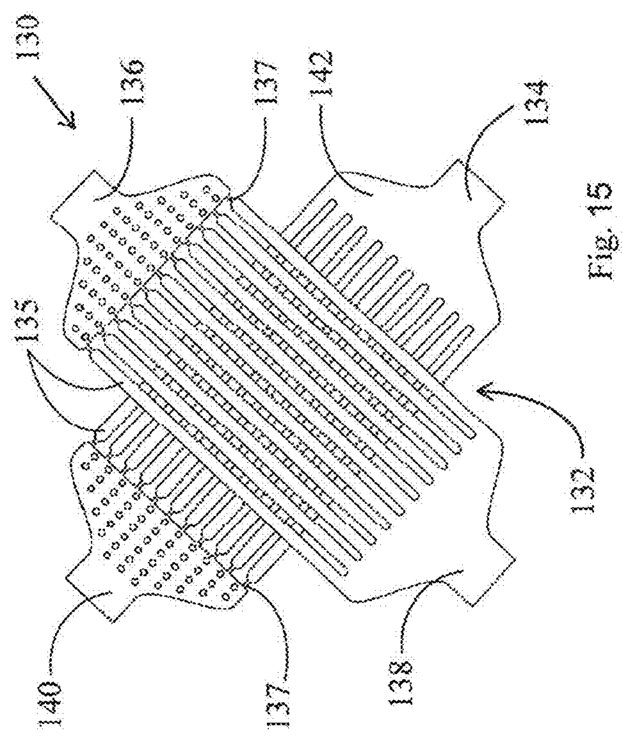
FIG. 15 shows a system for muscle stimulation for use in the sling of the invention.

FIG. 15 shows a multilayered mesh sling 130, in accordance with another embodiment of the invention for use in the treatment of POP. The mesh sling 130 comprises a top sling 132 and a bottom sling 134. The perforated ends 136 and 140 of the layers are adapted to be fixed by tissue ingrowth. The perforated ends 136 and 140 are connected to fingers 135 at connecting points 137. The fingered segment of each layer is removable by pulling this segment outward. The pulling causes a disconnection of the fingers from the permanent segment of the layer. The removable segment can be either inflatable or non-inflatable. The top sling 132 has a non-inflatable segment 136 and an inflatable segment 138. Similarly, the bottom sling 136 has a non-inflatable segment 140 and an inflatable segment 142. The layers of the sling can be snapped together and/or covered with biodegradable layers for early fixation.

The sling 130 can be mono-layered (wider than the suburethral slings and wider fixation ends) or multi-layered. The sling 130 can be removed by pulling its anterior end. The attachments detach from the narrow posterior end which remains attached to the posterior fixation tissues.

A sling of the invention, such as the sling 2_a_, shown in FIG. 1_a_, may be implanted, for example, using a trans-obturator approach, as shown in FIG. 16_a_, a transabdominal or trans-vaginal approach, as shown in FIG. 16_b_, or implanted as puborectal sling, as shown in FIG. 16_c_. The sling 2_a_ is implanted in an uninflated state as shown in FIG. 4. For implantation using the trans-oburator approach, shown in FIG. 16_a_, the sling is introduced into the body through incisions at the level of one of the obturator foramine and a midline vaginal incision under the urethra 120 and then through the contralateral obturator foramine before exiting the body through a second incision. The ports 8_a_ and 18_a_ thus remain outside the body after implantation. The tip of a syringe is inserted in to the valve of the port 8_a_ and the first element 4_a_ is inflated with an inflation fluid expelled from the syringe. The second element 6_a_ is inflated via the port 18_a_ with a similar amount of inflating material. At any time, the amount of inflation fluid inside the inflatable elements 4_a_ and 6_a_ can be changed in order to readjust the sling tension when it is determined that the urethra 120 is not supported in a desired manner.

The sling ends can have mesh-like segments for self fixation. If a trans-obturator approach is used the mesh ends should be over the obturator fascia. If an abdominal approach is used the mesh ends should be over the rectus fascia, where the mesh tips can be reached easily to be disconnected from the removable sling, in case the slings has to be removed.

The sling of the invention may be provided with a muscle stimulating device 130, shown schematically in FIG. 12 for stimulating periurethral and/or pelvic muscle contraction for reinforcing the mechanical effect of the sling during a sudden abdominal pressure increase. The stimulating device 130 comprises one or more pressure and/or motion sensors 132 that monitor the pressure and/or motion of the sling. Signals from the sensors are input to a processor 134. The processor 134 analyzes the sensor signals to detect a sudden increase in the pressure on the sling and/or a sudden increase in the motion of the sling. When a sudden increase in the pressure on the sling and/or a sudden increase in the motion of the sling is detected by the processor 134, the processor 134 activates one or more electrodes 136 that are implanted in one or more adjacent muscles, such the periurethral and/or the pelvic muscles. Activation of the electrodes 136 causes contraction of the muscles in which the electrodes are implanted. Contraction of the muscles reinforces the mechanical effect of the sling. The voltage across the electrodes may be generated from natural body motions and stored, for example, in a capacitor. Upon detection of a sudden motion, such as sneezing or coughing, the capacitor can be discharged across the electrodes.

When implanted, the sling of the invention may become encapsulated by fibrous tissue. However, unlike a mesh sling, the sling 2_a_ of the invention has a smooth surface which prevents invasion by the surrounding tissue. Spacing between adjacent finger-like projections in the sling allow vascularization of the tissues covering the sling. After encapsulation by fibrous tissue, the sling may be removed from the body, leaving behind the encapsulation which may function as an autologous sling.

At any time after implantation, the sling 2_a_ may be removed from the body. For removal, each of the ports 8_a_ and 18_a_ or sling ends are reached through respective skin incisions and grasped and the two ports or ends are simultaneously pulled away from the body. As the two ports are pulled apart, the connections 12 are disconnected so that the elements 4*a* and 6*a* become separated as they are removed from the body. The linear breaking strength of the disconnection points as measured by straight-pull tensile strength test of the sling may be higher than the suddenly increasing intra-abdominal pressure causing the urine or fecal leak to prevent its in-situ breakage. The smooth inner surface of the capsule and the smooth elements of the sling act as lubrication which facilitates removal of the elements from the body.

The invention claimed is:

1. An implantable sling comprising:

a) first and second opposing sling elements;

b) a plurality of elongated projections connecting said first and second opposing sling elements; and, c) wherein each said elongated projection comprises at least one connection structure for separating said elongated projection.

2. The sling according to claim 1 wherein each said connection structure is configured to tear when the first and the second sling elements are pulled apart.

3. The sling according to claim 2 wherein each said connection structure comprises at least one filament extending between the first and the second sling elements.

4. The sling according to claim 1 wherein one or both the first sling element and the second sling element is inflatable.

5. The sling according to claim 4 wherein an inflatable sling element has a port for introducing an inflation material into the inflatable sling element.

6. The sling according to claim 5 wherein a port of an inflatable sling element is positioned at a free end of the sling element.

7. The sling according to claim 1 comprising at least one of the following limitations:

(i) wherein the sling is made from an inelastic flexible material; and, (ii) wherein the sling has a smooth outer surface.

8. The sling according to claim 1 wherein the sling is embedded between layers of biodegradable or bioabsorbable mesh material.

9. The sling according to claim 8 wherein the layers of mesh are attached to one another by means of a snap-fit attachment.

10. The sling according to claim 1 wherein said elongated projections are at least one of are wires or first filaments.

11. The sling according to claim 10 wherein said at least one wire or filament of one of said first elongated projections is woven with said at least one wire or filament of a second elongated projection.

12. A system comprising a sling according to claim 1 and a muscle stimulating device.

13. The system according to claim 12 wherein the muscle stimulation device is configured to stimulate one or both of the periurethral and pelvic muscles.

14. The system according to claim 12 wherein the muscle stimulation device comprises:

(a) one or more sensors that are of a type selected from a pressure sensor and a motion sensor, the one or more sensors being configured to monitor the pressure on the sling or motion of the sling;

(b) one or more electrodes configured to be implanted in one or more selected from the periurethral and the pelvic muscles; and (c) a processor configured to:

(i) analyze signals from the sensors to detect a sudden increase in one or both of the pressure on the sling and a sudden increase in the motion of the sling; and (ii) when a sudden increase in one or both of the pressure on the sling and the motion of the sling is detected, activating the electrodes to cause contraction of the muscles in which the electrodes are implanted.

15. The system according to claim 14 further comprising means for:

(a) generating electrical energy from natural body movements;

(b) storing the electrical energy; and (c) activating the electrodes from the stored energy.

* * * * *